United States Patent [19]
Tedder

[11] Patent Number: 6,020,152
[45] Date of Patent: Feb. 1, 2000

[54] LYMPHOCYTE-ASSOCIATED CELL SURFACE PROTEIN

[75] Inventor: Thomas F. Tedder, Wellesley, Mass.

[73] Assignee: Dana-Farber Cancer Institute, Inc., Boston, Mass.

[21] Appl. No.: 08/036,453

[22] Filed: Mar. 24, 1993

Related U.S. Application Data

[62] Division of application No. 07/983,606, Nov. 30, 1992, which is a continuation of application No. 07/730,503, Jul. 8, 1991, abandoned, which is a continuation of application No. 07/313,109, Feb. 21, 1989, abandoned.

[51] Int. Cl.[7] .................................................. C12P 21/06
[52] U.S. Cl. .................. 435/69.1; 435/252.3; 435/320.1; 536/23.5
[58] Field of Search ............................... 435/69.1, 252.3, 435/320.1; 536/27

[56] References Cited

U.S. PATENT DOCUMENTS

| 4,783,330 | 11/1988 | Furie et al. ............................... 424/1.1 |
| 4,835,255 | 5/1989 | Weissman et al. ....................... 530/350 |
| 5,026,537 | 6/1991 | Daddona et al. .......................... 424/1.1 |
| 5,098,833 | 3/1992 | Lasky et al. ............................ 435/69.1 |
| 5,216,131 | 6/1993 | Lasky et al. ............................. 530/350 |
| 5,227,369 | 7/1993 | Rosen et al. ................................ 514/23 |

OTHER PUBLICATIONS

George et al. "Macromolecular Sequencing and Synthesis, Selected Methods and Applications", Alan R. Liss, Inc., chptr. 12, pp. 127–149, 1988.
Capon, D.J. et al., "Designing CD4 Immunoadhesions for AIDS Therapy," *Nature* 337, pp. 525–531 (1989).
Harlow, E. and D. Lane, *Antibodies: A Laboratory Manual*, Cold Spring Harbor Laboratory (1988), p. 287.
Harris et al., "Therapeutic Antibodies The Coming of Age," Tibtech, 3:99–121 (1993).
Kanof et al., "Induction of CD4 Suppressor T Cells With Anti–Leu–8 Antibody," J. Immunol. 139:49–64 (1988).
Mountz, J.D. et al., "Prevention of Lymphadenopathy In MRL–Ipr/Ipr Mice By Blocking Peripheral Lymph Node Homing With MEL–14 In Vivo," *J. Immunol.*, 140, pp. 2943–2949 (1988).
Reeck, G.R., et al., "'Homology' In Proteins and Nucleic Acids: A Terminology Muddle and a Way Out of It," *Cell*, 50, p. 667 (1987).
Aizawa et al., "Molecular basis of the recognition of intraveneously transplanted hemopoietic cells by bone marrow," Proc. Natl. Acad. Sci. USA 85:3180–3183 (1988).
Bargatze et al., "High Endothelial Venule Binding as a Predictor of the Dissemination of Passaged Murine Lymphomas," J. Exp. Med. 166:1125–1131 (1987).
Berg et al., "Homing Receptors and Vascular Addressins: Cell Adhesion Molecules that Direct Lymphocyte Traffic," Immunol. Rev. 108:421–427 (1989).
Bevilacqua et al., "Endothelial Leukocyte Adhesion Molecule 1: An Inducible Receptor for Neutrophils Related to Complement Regulatory Proteins and Lectins," Science 243:1160–1165 (1989).
Bevilacqua et al., "Identification of an inducible endothelial–leukocyte adhesion molecule," Proc. Natl. Acad. Sci. USA 84:9238–9242 (1987).
Bowen et al., "Characterization of a Human Homologue of the Murine Peripheral Lymph Node Homing Receptor," J. Cell Biol. 109:421–427 (1989).

(List continued on next page.)

*Primary Examiner*—John Ulm
*Attorney, Agent, or Firm*—Fish & Neave; James F. Haley, Jr., Esq.; Jane T. Gunnison, Esq.

[57] ABSTRACT

A human cDNA sequence encoding lymphocyte-associated cell surface protein LAM-1, which contains domains homologous with binding domains of animal lectins, growth factors, and C3/C4 binding proteins, and the LAM-1 protein encoded by the cDNA sequence, are described. Antagonists to LAM-1 are used in a method of treating a human patient suffering from a lymphocyte-mobilizing condition which involves administering a therapeutic amount of the antagonist in a non-tox pharmaceutical carrier substance.

8 Claims, 6 Drawing Sheets

OTHER PUBLICATIONS

Butcher et al., "Lymphocyte Adherence to High Endothelial Venules: Characterization of a Modified In Vitro Assay, and Examination of the Binding of Syngenic and Allogenic Lymphocyte Populations," J. Immunol. 123:1996–2003 (1979).

Camerini et al., "Leu–8/TQ–1 is the human equivalent of the Mel–14 lymph node homing receptor," Nature 342:78–82 (1989).

Carbone et al., "Expression of Leu–8 Surface Antigen in B–Cell Lymphomas. Correlation with Other B–cell Markers," J. Pathol. 154:133–140 (1988).

Chin et al., "Lymphocyte Recognition of Lymph Node High Endothelium. I. Inhibition of In Vitro Binding by a Component of Thoracic duct Lymph," J. Immunol. 125:1764–1769 (1980).

Chin et al., "Lymphocyte Recognition of Lymph Node High Endothelium. II. Characterization of an In Vitro Inhibitory Factor Isolated by Antibody Affinity Chromatography," J. Immunol. 125:1770–1774 (1980).

Chin et al., "Lymphocyte Recognition of Lymph Node High Endothelium. V. Isolation of Adhesion Molecules from Lysates of Rat Lymphocytes," J. Immunol. 131:1368–1374 (1983).

Collins et al., "Structure and Chromosomal Location of the Gene for Endothelial–Leukocyte Adhesion Molecule 1," J. biol. chem. 266:2466–2473 (1991).

Dana et al., "Two Functional Domains in the Phagocyte Membrane Glycoprotein Mo1 Identified with Monoclonal Antibodies," J. Immunol. 137:3259–3263 (1986).

DiStefano et al., "Identification of a truncated form of the nerve growth factor receptor," Proc. Natl. Acad. Sci. USA 85:270–274 (1988).

Dowbenko et al., "Characterization of the Murine Homing Receptor Gene Reveals Correspondence between Protein Domains and coding Exons," Genomics 9:270–277 (1991).

Downing et al., "Ligand and Protein Kinase C Downmodulate the Colony Stimulating Factor 1 Receptor by Independent Mechanisms," Mol. cell. Biol. 9:2890–2896 (1989).

Drickamer et al., "Complete amino acid sequence of a membrane receptor for glycoproteins," J. Biol. Chem. 256:5827–5839 (1981).

Drickamer et al., "Two Distinct Classes of Carbohydrate–recognition Domains in Animal Lectins," J. Biol. Chem. 263:9557–9560 (1988).

Duijvestijn et al., "Mechanisms and regulation of lymphocyte migration," Immunol. today 10:23–28 (1989).

Ezekowitz et al., "A human mannose–binding protein is an acute–phase reactant that shares sequence homology with other vertebrate lectins," J. Exp. Med. 167:1034–1046 (1988).

Gallatin et al., "Lymphocyte Homing Receptors," Cell 44:673–680 (1986).

Gallatin et al., "A cell–surface molecule involved in organ–specific homing of lymphocytes," Nature 304:30–34 (1983).

Gatenby et al., "Dissection of Immunoregulatory Subpopulations of T Lymphocytes within the Helper and Suppressor Sublineages in Man," J. Immunol. 129:1997–2000 (1982).

Geng et al., "Rapid neutrophil adhesion to activated endothelium mediated by GMP–140," Nature 323:757–760 (1990).

Goldstein et al., "A Human Lymphocyte Homing Receptor, the Hermes Antigen, is Related to Catilage Proteogylcan Core and Link Proteins," Cell 56:1063–1072 (1989).

Gregory, "Isolation and structure of urogastrone and its relationship to epidermal growth factor," Nature 257:325–327 (1975).

Griffin et al., "Granulocyte–Macrophage Colony–Stimulating Factor and Other Cytokines Regulate Surface Expression of the Leukocyte Adhesion Molecule–1 on Human Neutrophils, Monocytes, and their Precursors," J. Immunol. 145:576–584 (1990).

Hallmann et al., "The peripheral lymph node homing receptor, LECAM–1, is involved in CD18–independent adhesion of human neutrophils to endothelium," Biochem. Biophys. Res. Comm. 174:236–243 (1991).

Hidaka et al., "Isoquinolinessulfonamides, Novel and Potent Inhibitors of Cyclic Nucleotide Dependent Protein Kinase and Protein Kinace C," Biochemistry 23:5036–5041 (1984).

Hildreth et al., "The Human Lymphocyte Function–Associated (HFLA) Antigen and a Related Macrophage Differentiation Antigen HMac–1): Functional Effects of Subunit–Specific Monoclonal Antibodies," J. Immunol. 134:3272–3280 (1985).

Ichinose et al., "Amino–Acid Sequence of the b Subunit of Human Factor XIII, a Protein Composed of Ten Repetitive Segments," Biochemistry 25:4633–4638 (1986).

Imai et al., "Identification of a carbohydrate–based endothelial ligand for a lymphocyte homing receptor," J. Cell Biol. 113:1213–1221 (1991).

Jalkanen et al., "Lymphocyte Recognition of High Endothelium: Antibodies to Distinct Epitopes of an 85–95–kD Glycoprotein Antigen Differentially Inhibit Lymphocyte Binding to Lymph Node, Mucosal, or Synovial Endothelial Cells," J. Cell Biol. 105:983–990 (1987).

Johnson, G.J., et al., "Thromboxane unresponsive dog platelets have an abnormal thromboxane $A_2$/prostaglandin $H_2$ receptor–linked G protein," Blood Suppl. 72:327A (1988).

Johnston, G.I., et al., "Cloning of GMP–140, a Granule Membrane Protein of Platelets and Endothelium: Sequence Similarity to Proteins Involved in Cell Adhesion and Inflammation," Cell 56:1033–1044 (1989).

Johnston, G.I., et al., "Structure of the Human Gene Encoding Granule Membrane Protein–140, a Member of the Selectin Family of Adhesion Receptors for Leukocytes," J. Biol. Chem. 265:21381–21385 (1990).

Jung et al., "Rapid Modulation of Homing Receptors ($gp90^{MEL-14}$) induced by Activators of Protein Kinase C," J. Immunol. 144:130–136 (1990).

Jutila et al., "Characterization of a Functionallly Important and Evolutionarily Well–Conserved Epitope Mapped to the Short Cnosensus Repeats of E–Selectin and L–Selectin," J. Exp. Med. 175:1565–1573 (1992).

Jutila et al., "Function and Regulation of the Neutrophil MEL–14 Antigen In Vivo: Comparison with LFA–1 and MAC–1," J. Immunol. 143:3318–3324 (1989).

Kanof et al., "Leu–8 Antigen Expression is Diminished During Cell Activation But Does Not Correlate With Effector Function of Activated T Lymphocytes," J. Immunol. 140:3701–3706 (1988).

Kansas et al., "Molecular Mapping of Functional Domains of the Leukocyte Receptor for Endothelium, LAM–1," J. Cell Biol. 114:351–358 (1991).

Kansas et al., "Expression of Adhesion Structures During B Cell Development in Man," J. Immunol. 142:3058–3062 (1989).

Kansas et al., "A Family of Cell–Surface Glycoproteins Defined by a Putative Anti–Endothelial Cell Receptor Antibody in Man," J. Immunol. 142:3050–3057 (1989).

Kansas et al., "Maturational and Functional Diversity of Human B Lymphocytes Delineated with Anti–Leu–8," J. Immunol. 134:3003–3006 (1985).

Kikutani et al., "Molecular Structure of Human Lymphocyte Receptor for Immunoglobulin E," Cell 47:657–665 (1986).

Kishimoto et al., "Antibodies Against Human Neutrophil LECAM–1 (LAM–1/Leu–8/DREG–56 Antigen) and Endothelial Cell ELAM–1 Inhibit a Common CD18–Independent Adhesion Pathway In Vitro," Blood 78:805–811 (1991).

Kishimoto et al., "Identification of a Human Peripheral Lymph Node Homing Receptor: A Rapidly Down–Regulated Adhesion Molecule," Proc. Natl. Acad. Sci. USA 87:2244–2248 (1990).

Kishimoto et al., "Neutrophil Mac–1 and MEL–14 Adhesion Proteins Inversely Regulated by Chmotactic Factors," Science 245:1238–1241 (1989).

Klickstein et al., "Human C3b/C4b Receptor (CR1): Demonstration of Long Homologous Repeating Domains That Are Composed of the Short Consensus Repeats Characteristic of C3/C4 Binding Proteins," J. Exp. Med. 165:1095–1112 (1987).

Kozak et al., "Point Mutations Define a Sequence Flanking the AUG Initiator Codon That Modulates Translation by Eukaryotic Ribosomes," Cell 44:283–292 (1986).

Krusius et al., "A Fibroblast Chondroitin Sulfate Proteoglycan Core Protein Contains Lectin–like and Growth Factor–like Sequences," J. Biol. Chem. 262:13120–13125 (1987).

Kurk et al., "Characterization of an Endothelial Cell Antigen Recognized by an Anti–Leukocyte Homing Receptor (L–Selectin) Monoclonal Antibody," FASEB J. 6:A1142 (1992).

Larsen et al., "Padgem–Dependent adhesion of platelets to monocytes and neutrophils is mediated by a lineage–specific carboyhydrate, LNF III (CD15),"Cell 63:467–474 (1990).

Larsen et al., "Padgem Protein: A receptor that mediates the Interaction of activated platelets with neutrophils and monocytes," Cell 59:305–312 (1989).

Lasky et al., "Cloning of a Lymphocyte Homing Receptor Reveals a Lectin Domain," Cell 56:1045–1055 (1989).

Lasky, "Selectins: Interpreters of Cell–Specific Carbohydrates Information During Inflammation," Science 258:964–969 (1992) (copy enclosed).

Leonard et al., "Molecular cloning and expression of cDNAs for the human interleukin–2 receptor," Nature 311:626–631 (1984).

Lewinsohn et al., "Leukocyte–endothelial cell recognition: Evidence of a common molecular mechanism shared by neutrophils, lymphoyctes, and other leukoyctes," J. Immunol. 138:4313–4321 (1987).

Ley et al., "Lectin–Like Cell Adhesion Molecule 1 Mediates Leukocyte Rolling in Mesenteric Venules In Vivo," Blood 77:2553–2555 (1991).

Luscinskas et al., "Cytokine–activated human endothelial monolayers support enhanced neutrophil transmigration via a mechanism involving both endothelial–leukocyte adhesion molecule–1 and intercellular adhesion molecule–1," J. Immunol. 146:1617–1625 (1989).

Luscinskas et al., "Endothelial–leukocyte adhesion molecule–1–dependent and leukocyte (CD11/CD18)–dependent mechanisms contribute to polymorphonuclear leukocyte adhesion to cytokine–activated human vascular endothelium," J. Immunol. 142:2257–2263 (1989).

Marx, "New Family of Adhesion Proteins Discovered," Science 243:1144 (1989).

Michie et al., "Expression of the Leu–8 Antigen by B–Cell Lymphomas," Am. J. Clin. Pathol. 88:486–490 (1987).

Miyake et al., "Hyaluronate Can Function as a Cell Adhesion Molecule and CD44 Participates in Hyaluronate Recognition," J. Exp. Med. 172:69–75 (1990).

Morley et al., "Internal homologies of the Ba fragment from human complement component Factor B, a class III MHC angtigen," EMBO J. 3:153–157 (1984).

Nojima et al., "VLA–4 Mediates CD3–dependent $CD4^+$ T Cell Activation Via the CS1 Alternatively Spliced Domain of Fibronectin," J. Exp. Med. 172:1185–1192 (1990).

Ord et al., "Structure of the Gene Encoding the Human Leukocyte Adhesion Molecule–1 (TQ1, Leu–8) of Lymphocytes and Neutrophils," J. Biol. Chem. 265:7760–7767 (1990).

Osborn, "Leukocyte Adhesion to Endothelium in Inflammation," Cell 62:3–6 (1990).

Pals et al., "Expression of Lymphocyte Homing Receptor as a Mechanism of Dissemination in Non–Hodgkins's Lymphoma," Blood 73:885–888 (1989).

Picker et al., "The Neutrophil Selectin LECAM–1 Presents Carbohydrate Ligands to the Vascular Selectins ELAM–1 and GMP–140," Cell 66:921–933 (1991).

Polte et al., "Full length vascular cell adhesion molecule 1 (VCAM–1)," Nuc. Acids Res. 18:5901 (1990).

Porteau et al., "Shedding of Tumor Necrosis Factor Receptors by Activated Human Neutrophils," J. Exp. Med. 172:599–607 (1990).

Reinherz et al., "Heterogeneity of Human T4 Inducer T cells Defined by a Monoclonal Antibody that Delineates Two Functional Subpopulations," J. Immunol. 128:463–468 (1982).

Rice et al., "Vascular and Nonvascular Expression of INCAM–110," Amer. J. Pathol. 138:385–393 (1991).

Rice et al., "An Inducible Endothelial Cell Surface Glycoprotein Mediates Melanoma Adhesion," Science 246:1303–1306 (1989).

Rosen et al., "Involvement of Sialic Acid on Endothelial Cells in Organ–Specific Lymphocyte Recirculation," Science 228:1005–1007 (1985).

Rothlein et al., "A Human Intercellular Adhesion Molecule (ICAM–1) Distinct From LFA–1," J. Immunol. 137:1270–1274 (1986).

Rothlein et al., "A Form of Circulating ICAM–1 in Human Serum," J. Immunol. 147:3788–3793 (1991).

Sanchez–Madrid et al., "Three distinct antigens associated with human T–lymphocyte–mediated cytolysis: LFA–1, LFA–2, and LFA–3," Proc. Natl. Acad. Sci. USA 79:7489–7493 (1982).

Sher et al., "Homing Receptors and Metastasis," Adv. Can. Res. 51:361–389 (1988).

Siegelman et al., "The mouse lymph node homing receptor is identical with the lymphocyte cell surface marker Ly–22: Role of the EGF domain in endothelial binding," Cell 61:611–622 (1990).

Siegelman et al., "Human homologue of mouse lymph node homing receptor: Evolutionary conservation at tandem cell interaction domains," Proc. Natl. Acad. Sci. USA 86:5562–5566 (1989).

Siegelman et al., "Mouse Lymph Node Homing Receptor cDNA Clone Encodes a Glycoprotein Revealing Tandem Interactions Domains," Science 243:1165–1172 (1989).

Smith et al., "Chemotactic factors regulate lectin adhesion molecule 1 (LECAM–1)–dependent neutrophil adhesion to cytokine–stimulated endothelial cells In Vitro," J. Clin. Invest. 87:609–618 (1991).

Spertini et al., "Function and Evolutionary Conservation of Distinct Epitopes on the Leukocyte Adhesion Molecule–1 (TQ–1, Leu–8) that Regulate Leukocyte Migration," J. Immunol. 147:942–949 (1991).

Spertini et al., "Leukocyte Adhesion Molecule (LAM–1, L–Selectin) Interacts with an Inducible Endothelial Cell Ligand to Support Leukocyte Adhesion," J. Immunol. 147:2565–2573 (1991).

Spertini et al., "Regulation of Leukocyte Adhesion Molecule–1 (TQ1, Leu–8) Expression and Shedding by Normal and Malignant Cells," Leukemia 5:300–308 (1991).

Spertini et al., "Regulation of leukocyte migration by activation of the leukocyte adhesion molecule–1 (LAM–1) selectin," Nature 349:691–694 (1991).

Spiess et al., "Sequence of a Second Human Asialoglycoprotein Receptor: conservation of Two Receptor Genes During Evolution," Proc. Natl. Acad. Sci. USA 82:6465–6469 (1985).

Springer, "Adhesion receptors of the immune system," Nature 346:425–434 (1990).

Stamekovic et al., "A Lymphocyte Molecule Implicated in Lymph Node Homing is a Member of the Cartilage Link Protein Family," Cell 56:1057–1062 (1989).

Stamper et al., "Lymphocyte Homing into Lymph Nodes: In Vitro Demonstration of the Selective Affinity of Recirculating Lymphocytes for High–Endothelial Venules," J. Exp. Med. 144:828–833 (1976).

Stoolman et al., "Homing Receptors on Human and Rodent Lymphoyctes—Evidence for a Conserved Carbohydrate–Binding Specificity," Blood 70:1842–1850 (1987).

Stoolman, "Adhesion Molecules Controlling Lymphocyte Migration," Cell 56:907–910 (1989).

Stoolman et al., "Phosphomannosyl Receptors May Participate in the Adhesive Interaction between Lymphocytes and High Endothelial Venules," J. Cell Biol. 99:1535–1540 (1984).

Stoolman et al., "Adhesion Molecules of Cultured Hematopoietic Malignancies," J. Clin. Invest. 84:1196–1205 (1989).

Strickler et al., "Intermediate Lymphocytic Lymphoma: An Immunophenotypic Study with Comparison to Small Lymphocytic Lymphoma and Diffuse Small Cleaved Cell Lymphoma," Hum. Path. 19:550–554 (1988).

Takahashi et al., "Cloning and Sequencing of cDNA of *Sarcophaga perengrina* Humoral Lectin Induced on Injury of the Body Wall," J. Biol. Chem. 260:12228–12233 (1985).

Tamaoki et al., "Staurosporine, A Potent Inhibitor of Phospholipid/$Ca^{++}$ Dependent Protein Kinase," Biochem. Biophys. Res. Comm. 135:397–402 (1986).

Tedder, "Cell–surface Receptor Shedding: A Means of Regulating Function," Am. J. Respir. Cell Mol. Biol. 5:305–307 (1991).

Tedder et al., "Function of the LFA–1 and T4 molecules in the direct activation of resting human B lymphocytes by T lymphocytes," Eur. J. Immunol. 16:1539–1543 (1986).

Tedder et al., "Human antigen–specific memory T cells express the homing receptor (LAM–1) necessary for lymphocyte recirculation," Eur. J. Immunol. 20:1351–1355 (1990).

Tedder et al., "Isolation and Chromosomal Localization of cDNAs Encoding a Novel Human Lymphocyte Cell Surface Molecule, LAM–1," J. Exp. Med. 170:123–133 (1989).

Tedder et al., "Human Lymphocyte Differentiation Antigens HB–10 and HB–11," J. Immunol. 134:2989–2994 (1985).

Tedder et al., "Expression of the Human Leukocyte Adhesion Molecule, LAM–1: Identity with the TQ1 and Leu–8 Differentiation Antigens," J. Immunol. 144:532–540 (1990).

Tedder et al., "Heterogeneity in the B1 (CD20) Cell Surface Molecule Expressed by Human B–Lymphocytes," Molecular Immunol. 25:1321–1330 (1988).

Tedder et al., "Isolation and structure of a cDNA encoding the B1 (CD20) cell–surface antigen of human B lymphocytes," Proc. Natl. Acad. Sci. USA 85:208–212 (1988).

True et al., "Requirement for Sialic Acid on the Endothelial Ligand of a Lymphocyte Homing Receptor," J. Cell Biol. 111:2757–2764 (1990).

von Haijne, "A New Method for Predicting Signal Sequence Cleavage Sites," Nucleic Acid Research 14:4683–4690 (1986).

Walcheck et al., "Characterization of the Bovine Peripheral Lymph Node Homing Receptor: A Lectin Cell Adhesion Molecule (LECAM)," Eur. J. Immunol. 22:469–476 (1992).

Watson, M. et al., "Genomic Organization of the Selectin Family of Leukocyte Adhesion Molecules on Human and Mouse Chromosome 1", J. Exp. Med. 172:263–272 (1990).

Watson, S. et al., "A Homing Receptor–IgG Chimera as a Probe for Adhesive Ligands of Lymph Node High Endothelial Venules," J. Cell Biol. 110:2221–2229 (1990).

Watson, S. et al., "The complement binding–like domains of the murine homing receptor facilitate lectin activity," J. Cell Biol. 115:235–243 (1991).

Watson, S. et al., "Neutrophil influx into an inflammatory site inhibited by a soluble homing receptor–IgG chimera," Nature 349:164–167 (1991).

Weiss et al., "Interactions of cancer cells with the microvasculature during metastasis," FASEB J. 2:12–21 (1988).

Wu et al., "Evolutionary Conservation of Tissue–specific Lymphocyte–Endothelial Cell Recognition Mechanisms Involved in Lymphyocyte Homing," J. Cell Biol. 107:1845–1851 (1988).

Yednock et al., "Phosphomannosyl–derivatized Beads Detect a Receptor Involved in Lymphocyte Homing," J. Cell Biol. 104:713–723 (1987).

Yednock et al., "Receptors Involved in Lymphocyte Homing: Relationship between a Carbohydrate–binding Receptor and the MEL–14 Antigen," J. Cell Biol. 104:725–731 (1987).

Yoshitake et al., "Nucleotide Sequence of the Gene for Human Factor IX (Antihemophilic Factor B)," Biochemistry 25:3736–3750 (1985).

```
                                                               1
                                                               M   G
gaattcCCTTT GGGCAAGGAC CTGAGACCCT TGTGCTAAGTCAAGAGGCTCA ATG GGC
                              10
 C   R   R   T   R   E   G   P   S   K   A   M
TGC AGA AGA ACT AGA GAA GGA CCA AGC AAA GCC ATG                  94
                    20
 I   F   P   W   K   C   Q   S   T   Q   R   D   L   W   N   I
ATA TTT CCA TGG AAA TGT CAG AGC ACC CAG AGG GAC TTA TGG AAC ATC  30

F   K   L   W   G   W   T   M   L   C   C   D
TTC AAG TTG TGG GGG TGG ACA ATG CTC TGT TGT GAT                  168
                                        40
 F   L   A   H   H   G   T   D   C   W   T   Y   H   Y   S   E
TTC CTG GCA CAT CAT GGA ACC GAC TGC TGG ACT TAC CAT TAT TCT GAA
                                    50

K   P   M   N   W   Q   N   W   R   A   R   F   C
AAA CCC ATG AAC TGG CAA AAC TGG AGA GCT AGA AGA TTC TGC          262
 60                                                80

R   D   N   Y   T   T   D   L   V   A   I   Q   N   K   A   E   I
CGA GAC AAT TAC ACA GAT TTA GTT GCC ATA CAA AAC AAG GCG GAA ATT
                90

E   Y   L   E   K   T   L   P   F   S   R   S
GAG TAT CTG GAG AAG ACT CTG CCT TTC AGT CGT TCT                  346
```

FIG. 2A

```
        100                                              110
 Y   Y   W   I   G   I   R   K   I   G   G   I   W   T   W
TAC TAC TGG ATA GGA ATC CGG AAG ATA GGA GGA ATA TGG ACG TGG
                                120
 V   G   T  |N   K   S | L   T   E   E   A   E   N
GTG GGA ACC |AAC AAA TCT| CTC ACT GAA GAA GCA GAG AAC  430
            130                                          140
 W   G   D   G   E   P   N   N   K   K   N   K   E   D   C
TGG GGA GAT GGT GAG CCC AAC AAC AAG AAG AAC AAG GAG GAC TGC
                                    150
 V   E   I   Y   I   K   R   N   K   D   A   G   K
GTG GAG ATC TAT ATC AAG AGA AAC AAA GAT GCA GGC AAA  514
                        160
 W   N   D   D   A   C   H   K   L   K   A   A   L   C   Y
TGG AAC GAT GAC GCC TGC CAC AAA CTA AAG GCA GCC CTC TGT TAC
170                                              180
 T   A   S   C   Q   P   W   S   C   S   G   H   G
ACA GCT TCT TGC CAG CCC TGG TCA TGC AGT GGC CAT GGA  598
                            190
 E   C   V   E   I   I   N  |N   Y   T | C   N   C   D   V
GAA TGT GTA GAA ATC ATC AAT |AAT TAC ACC| TGC AAC TGT GAT GTG
                200                                      210
 G   Y   Y   G   P   Q   C   Q   F   V   I   Q   C
GGG TAC TAT GGG CCC CAG TGT CAG TTT GTG ATT CAG TGT  682
                                220
 E   P   L   E   A   P   E   L   G   T   M   D   C   T   H
GAG CCT TTG GAG GCC CCA GAG CTG GGT ACC ATG GAC TGT ACT CAC
                    230
 P   L   G   N   F   N   F   N   S   Q   C   A   F
CCT TTG GGA AAC TTC AAC TTC AAC TCA CAG TGT GCC TTC  766
240                                          250
 S   C   S   E   G   T  |N   L   T | G   I   E   E   T   T
AGC TGC TCT GAA GGA ACA |AAC TTA ACT| GGG ATT GAA GAA ACC ACC
                         260
 C   E   P   F   G  |N   W   S | S   P   E   P   T
TGT GAA CCA TTT GGA |AAC TGG TCA| TCT CCA GAA CCA ACC  850
                270                                      280
 C   Q   V   I   Q   C   E   P   L   S   A   P   D   L   G
TGT CAA GTG ATT CAG TGT GAG CCT CTA TCA GCA CCA GAT TTG GGG
                                290
 I   M  |N   C   S | H   P   L   A   S   F   S   F
ATC ATG |AAC TGT AGC| CAT CCC CTG GCC AGC TTC AGC TTT  934
         300
 T   S   A   C   T   F   I   C   S   E   G   T   E   L   I
ACC TCT GCA TGT ACC TTC ATC TGC TCA GAA GGA ACT GAG TTA ATT
310                                          320
 G   K   K   K   T   I   C   E   S   S   G   I   W
GGG AAG AAG AAA ACC ATT TGT GAA TCA TCT GGA ATC TGG  1018
                                330
 S  |N   P   S | P   I   C   Q   K   L   D   K   S   F   S
TCA |AAT CCT AGT| CCA ATA TGT CAA AAA TTG GAC AAA AGT TTC TCA
     340                                         350
 M   I   K   E   G   D   Y   N   P   L   F   I   P
ATG ATT AAG GAG GGT GAT TAT AAC CCC CTC TTC ATT CCA  1102
```

FIG. 2B

```
                                    360
V   A   V   M   V   T   A   F   S   G   L   A   F   I   I
GTG GCA GTC ATG GTT ACT GCA TTC TCT GGG TTG GCA TTT ATC ATT
                        370
W   L   A   R   R   L   K   K   G   K   K   S   K
TGG CTG GCA AGG AGA TTA AAA AAA GGC AAG AAA TCC AAG        1186
        380
R   S   M   N   D   P   Y   *
AGA AGT ATG AAT GAC CCA TAT TAA ATCGCCCTTG GTGAAAGAAA
```

ATTCTTGGAA TACTAAAAAT CATGAGATCC TTTAAATCCT TCCATGAAAC 1280

GTTTTGTGTG GTGGCACCTC CTACGTCAAA CATGAAGTGT GTTTCCTTCA

GTGCATCTGG GAAGATTTCT ACCTGACCAA GAGTTCCTTC AGCTTCCATT 1380

TCACCCCTCA TTTATCCCTC AACCCCAGC CCACAGGTCT TTATACAGCT

CAGCTTTTTC TCTTTTCTGA GGAGAAACAA ATAACACCAT AAAGGGAAAG 1480

GATTCATGTG GAATATAAAG ATGGCTGACT TTGCTCTTTC TTGACTCTTG

TTTTCAGTTT CAATTCAGTG CTGTACTTGA TGACAGACAC TTCTAAATGA 1580

AGTGCAAATT TGATACATAT GTGAATATGG ACTCAGTTTT CTTGCAGATC

AAATTTCGCG TCGTCTTCTG TATACGTCCA GGTACACTCT ATGAAGTCAA 1680

AAGTCTACGC TCTCCTTTCT TTCTAACTCC AGTGAAGTAA TGGGGTCCTG

CTCAAGTTGA AAGAGTCCTA TTTGCACTGT AGCCTCGCCG TCTGTGAATT 1780

GGACCATCCT ATTTAACTGG CTTCAGCCTC CCCACCTTCT TCAGCCACCT

CTCTTTTTCA GTTGGCTGAC TTCCACACCT AGCATCTCAT GAGTGCCAAG 1880

CAAAAGGAGA GAAGAGAGAA ATAGCCTCCG CTGTTTTTA GTTTGGGGGT

TTTGCTGTTT CCTTTTATGA GACCCATTCC TATTTCTTAT AGTCAATGTT 1980

TCTTTTATCA CGATATTATT AGTAAGAAAA CATCACTGAA ATGCTAGCTG

CAACTGACAT CTCTTTGATG TCATATGGAA GAGTTAAAAC AGGTGGAGAA 2080

ATTCCTTGAT TCACAATGAA ATGCTCTCCT TTCCCCTGCC CCCAGACCTT

TTATCCACTT ACCTAGATTC TACATATTCT TTAAATTTCA TCTCAGGCCT 2180

CCCTCAACCC CACCACTTCT TTTATAACTA GTCCTTTACT AATCCAACCC

ATGATGAGCT CCTCTTCCTG GCTTCTTACT GAAAGGTTAC CCTGTAACAT 2280

GCAATTTTGC ATTTGAATAA AGCCTGCTTT TTAAGTGTTA AAAAgaattc 2330

```
LAM-1    35  GWWMLCC-DFLAHHGTDCWTHYSEKPMNWQRARRFCRNDYTDLVAIQN-
FcE-R   175  GFVCNTCPEKWINFQRKC---MYPGLGTKQWVHARYACDDMEGQLVSIHS-
C-HL     75  LFPCGAQSRQWEYFEGRC---LYFSLSRMSWHKAKAECEEMHSHIIIDS-
H-MBP   118  NGTYQKCLTESLGKQVNLFFLTNGE-IMIFELVLALC-VKFQPLWPPPG-
F-PGC   452  GQDTETCDYGWHKFQGQC---YKYFAHRRIWDAAERECRLQGAHITSILS-
HHL-1   148  GSERTCCPVNWEHERSC---MWPSRSGKAWADADNYCRLENAHLVAVTS-
ISL      17  IFIISTAAVPQLRKALDGREYLIETELKYNWHQAWHECARHDQQLVTIESA

LAM-1        --KAETEYLEKTIPFSRSYYWIGIRKIG-----GIMIWV-GINKSLTEEAENW-
FcE-R        --PEE----QDFLITLHASHTGSWIGIRNLDLK---GEFIWVDGSHVD---YSNW
C-HL         --YAK----QNFVMFRTRNERFWIGLTDENQE---GEWVDGIDTRSS---FTFW
H-MBP        --MAA----EKGAIQNLILEEAFLGMPDELTE---GQF--MDLIIGNRLT---YTNW
F-PGC        --HEE----QMFVNRVGHDYQ-WIGLNDKMFE---HDERWIDGS---ILQYENW
HHL-1        --WEE----QKPVQHHIGPVNTWMGLHDQN----GPWKWVDGIDYE-IG-PKNW
ISL          DKNNAIDLIVKRVVGKSHNLWLGNDEYSRDYGPFFWS-PIGQAFS--FAYW

LAM-1        GDGEPNNKKNK-------EDCVELYIKRNKDAGKWNDDACH-KLKAALCYI  160
FcE-R        APGEPTSRSQ--G-----EDCVVM--R----GSGRWNDAFCDRKLGAWVCDR  284
C-HL         LEGEPNNR-------G--FNEDCAH------VWTSGQWNDVYCTYECYY-VCEL  203
H-MBP        NEGEPNNA----------GSDEHCVL-----LLKNGQWNDSPCF--HIPSAVCEF  245
F-PGC        RPNQPDSFFSA--G----EDCVVI-I----WHENGQWNDVPQNYHLTY-TCKK  580
HHL-1        RPEQPDDWYGHGLGGGEDCAH----PTDGRWNDDVCQ--RPYRWVCEII  279
ISL          SENNPNNYLHQ-------EICVHIWNTLPLY--QWNDDDCN-VIMGYICEP  159
```

```
LAM-1  173  CQP - - - WSCSGHGECVEIIN - - -YTCNCDVGYYGPCQ    205
EGF      6  CPLSHDGYCLHDGVCMYIEALDKYACNCVVGYIGERCQ           43
F-IX    51  CES - - - NPCLNGGSCKDDINS - -YECWCPFGFEGKNCE     83
F-PGCP 382  CKM - - - NPCKNGGTCYPTETS - -YVCTCVPGYSGDQCE    414
```

FIG. 3B

```
         *   +                                             +
LAM-1  207  VIQCEPLEAPELGTMDCTHPLGNFN - SQCAF - - -         268
LAM-1  269  VIQCEPLSAPDLGIMNCSHPLASFT - SACTF - - -         330
Ba     137  AGYCSNPGIP - IGTRKVGSQYRLED - SV - TY - - -     194
CR1    694  CQPPEILH - GEHTPSHQD - NFS - PGQEVFY - - -      751
IL-2R  101  PGHCREPP - PWENEATERIYHFVVG - QMVYYQ - - -      164
F-XIII   1  EKPCGFPHVENGRIAQYYYTFKSFYEPMSIDKKLSF             68
```

FIG. 3C

```
         *
LAM-1    SCSEGTN - - L - TGIEE - TTC - - - EPFGNWSSPEPTCQ    268
LAM-1    ICSEGTE - - L - IGKKK - TIC - - - ESSGIWSNPSPICQ    330
Ba       HCSRGLT - - L - RGSQR - RTC - - - QEGGSWSGTEPSCQ    194
CR1      SCEPGYD - L - RGAAS - LHC - - - TPQGDWSDEAPRCA      751
         *
IL-2R  - CVQGYRALHRGPAE - SVCKMTHGKTRWTQPQLICT                164
F-XIII   FCLAGYYTTESSRQEEQTTCT - TE - - - WS - PEPRCF        68
```

FIG. 3C

LYMPHOCYTE-ASSOCIATED CELL SURFACE PROTEIN

This application is a division of application Ser. No. 07/983,606, filed Nov. 30, 1992, which is a continuation of application Ser. No. 07/730,503, filed Jul. 8, 1991 (now abandoned), which is a continuation of application Ser. No. 07/313,109, filed Feb. 21, 1989, also abandoned.

The invention was made with Government support of the Government has certain right in this invention under grants from the National Institutes of Health CA-34183 and AI-26872.

The invention relates to human lymphocyte-associated cell surface proteins.

BACKGROUND OF THE INVENTION

Genes exclusively expressed by one cell lineage, but not by others, often define the function of that cell population. The generation of genes by the assembly of functionally independent domains has occurred frequently as new genes have evolved to encode proteins with new functions. An inducible endothelial-leukocyte adhesion molecule (ELAM-1) is expressed on the surface of cytokine-treated endothelial cells. This molecule is thought to be responsible for the accumulation of blood leukocytes at sites of inflammation by mediating the adhesion of cells to the vascular lining (Bevilacqua et al., Proc. Natl. Acad. Sci. USA 84:9238 (1987)). A granule membrane protein found in platelets and endothelial cells, termed GMP-140, has been cloned and is homologous with ELAM-1 (Johnston et al., Blood Suppl. 1 72:327A (1988)).

SUMMARY OF THE INVENTION

Figure 2A:
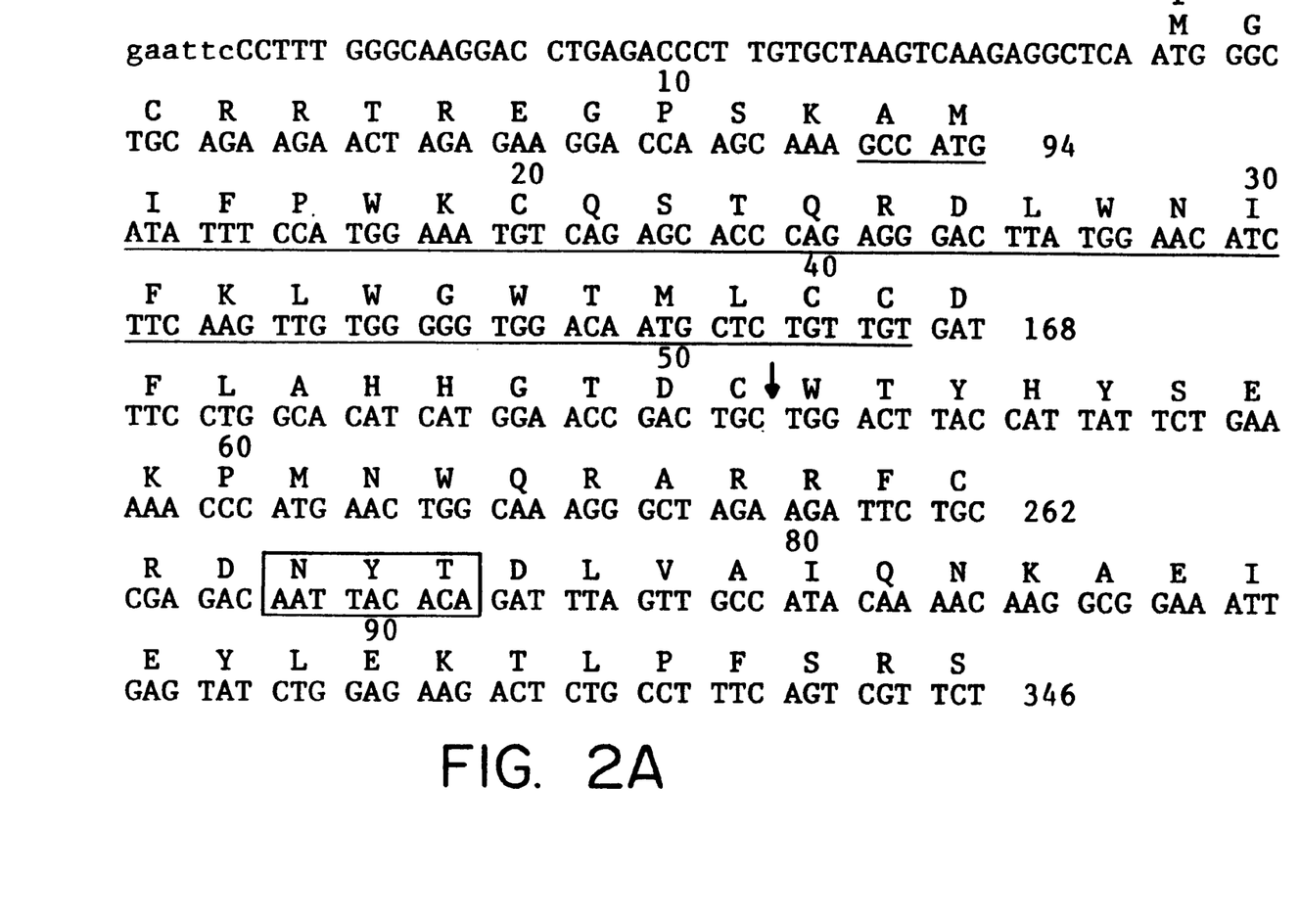

The invention generally features a human cDNA sequence encoding lymphocyte-associated cell surface protein LAM-1, which contains domains homologous with binding domains of animal lectins, growth factors, and C3/C4 binding proteins; and the LAM-1 protein encoded by the cDNA sequence or an immunogenic fragment of LAM-1. In a preferred embodiment, the cDNA sequence is isolated from a population of B cell-specific cDNAs from a human tonsil cDNA library, and the amino acid sequence of the protein is substantially as indicated in FIG. 2, more preferably 80% homologous with the sequence shown in FIG. 2 and most preferably 90% homologous. (Here "substantially as indicated" defines a sequence close enough to the indicated sequence to have the same function.)

In another aspect, the invention features antibody developed against lymphocyte-associated cell surface protein LAM-1, or a fragment thereof, or against a molecule that specifically associates with LAM-1, or a fragment thereof, to generate a functional molecule.

In another aspect, the invention features a method of identifying cells that express LAM-1 which involves reacting the antibody just described with a population of cells and isolating those that bind the antibody. Binding of antibody can also be used to block the receptor activity of LAM-1.

In another aspect, the invention features a method of treating a human patient suffering from a lymphocyte-mobilizing condition which involves administering a therapeutic amount of an antagonist to LAM-1 in a non-toxic pharmaceutical carrier substance. In preferred embodiments of the method the patient is suffering from tissue damage, an autoimmune disorder, or cancer, or the patient is an organ or tissue transplant recipient.

In another aspect, the invention features using the cDNA sequence defined above to isolate cross-hybridizing human DNAs.

In another aspect the invention features using LAM-1 to identify a ligand which will bind to it or to a molecule that is specifically associated with LAM-1 to generate a functional molecule.

As used herein the term antagonist includes any agent which interacts with LAM-1 and interferes with its function, eg., antibody reactive with LAM-1 or any ligand which binds to LAM-1.

Lymphocyte-associated cell surface protein LAM-1 is a unique receptor protein which has not previously been identified. LAM-1 contains domains that are homologous with those found in several different receptors and is a newly described member of a gene family that includes ELAM-1 and GMP-140, proteins which have been implicated in cell adhesion. LAM-1 most likely serves a similar function but is uniquely expressed by lymphocytes. The isolation of cDNA encoding LAM-1 has allowed the determination of the structure of this molecule; the cDNA has been used to transfer expression of LAM-1 to cells that do not express this gene.

Antibodies reactive with LAM-1 can be used to identify cells that express this receptor and to block its function. In addition, the cDNA protein product can be used to develop antagonistic ligands that can interfere with lymphocyte adhesion and function and thereby be used to treat such conditions as tissue damage and metastasis of cancer cells.

Other features and advantages of the invention will be apparent from the following description of the preferred embodiments thereof and from the claims.

In the drawings.

FIGS. 2a–2c shows the determined cDNA nucleotide sequence and the deduced amino acid sequence of LAM-1.

B cell-specific cDNAs were isolated from a human tonsil cDNA library (ATCC #37546) using differential hybridization with labeled cDNAs derived from either B cell (RAJI) RNA or T cell (HSB-2) RNA (Tedder et al., Proc. Natl. Acad. Sci. USA 85:208–212 (1988)). Positive plaques were isolated and cloned, and the cDNA inserts were subcloned into the plasmid pSP65 (Promega, Madison, Wis.). Nucleotide sequences were determined using the method of Maxam and Gilbert (Meth. Enzymol. 65:499 (1980)). Gap penalties of –1 were assessed during homology analysis for each nucleotide or amino acid in the sequence where a gap or deletion occurred. One of the 261 RAJI+ HSB2– cDNA clones isolated, B125, contained a 1.90 kb cDNA insert that hybridized with a 2.4 kb RNA species found in several B cell lines (Tedder et al., supra). However, B125 did not hybridize with any of the other RAJI+HSB2– clones or with mRNA from several T cell lines. The B125 cDNA clone was characterized by restriction mapping and nucleotide sequence determination. A near-full-length 2.3 kb cDNA that hybridized with B125 was isolated, sequenced, and termed pLAM-1.

Figure 1A:
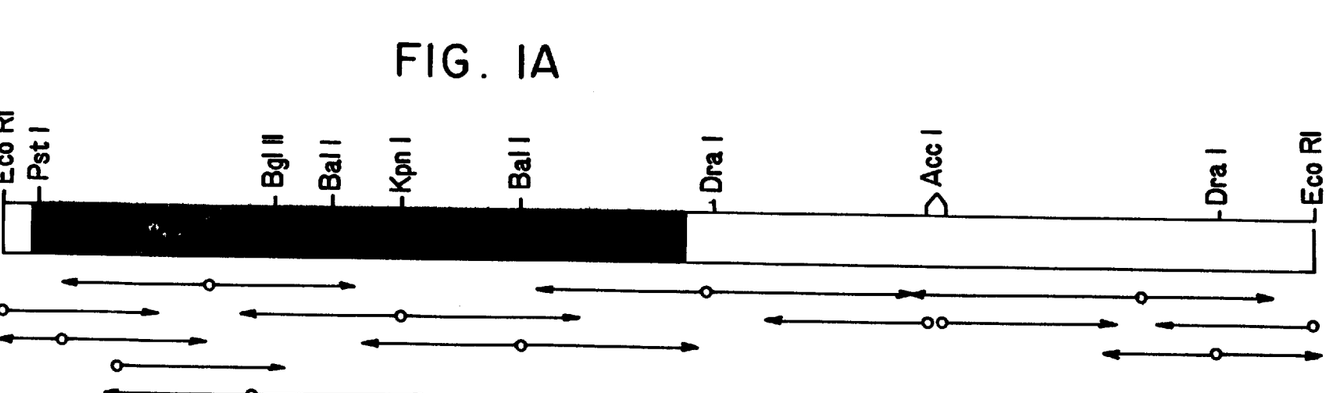
FIGS. 1A and 1B show the structure of the LAM-1 cDNA clone.
Figure 1B:
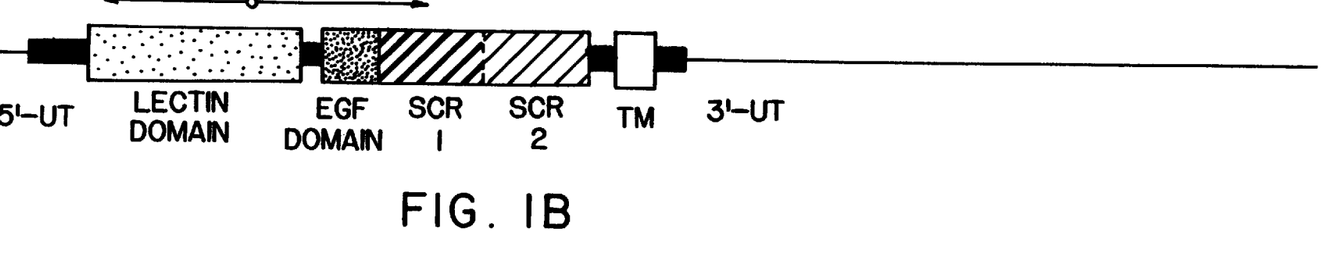

As shown in FIG. 1A, a restriction map was constructed by the standard single, double or triple digestions of pLAM-1. The putative coding region is shown in black. Arrows indicate the direction and extent of nucleotide sequence determination and the open circles indicate 5'-end labeling. In FIG. 1B, a schematic model of the structure of the LAM-1 mRNA is shown. Thin lines indicate 5' and 3' untranslated sequences (UT), while the thick bar indicates the translated region. The boxes represent the lectin-like and epidermal growth factor (EGF)-like domains and the two short consensus repeat (SCR) units. The open box indicates the putative transmembrane (TM) region.

The expression of LAM-1 mRNA by cell lines of lymphoid and non-lymphoid origin was examined. Northern blot analysis revealed that LAM-1 hybridized strongly to a 2.6 kb RNA species and weakly to a 1.7 kb RNA species in poly(A)+RNA isolated from the B cell lines Raji, SB, Laz-509, and GK-5. However, RNA isolated from two pre-B cell lines (Nalm-6, PB-697), three B cell lines (Namalwa, Daudi, BJAB), five T cell lines (CEM, Hut-78, HSB-2, Molt-15, Molt-3), a myelomonocytic cell line (U937 and U937 cultured with LPS) and erythroleukemic (K-562) cell line did not hybridize with LAM-1 suggesting that expression of this gene was preferentially associated with B lymphocytes.

The B125 cDNA clone contained an 1,181 bp open reading frame that could encode a protein of 372 amino acids as shown in FIG. 2. The numbers shown above the amino acid sequence designate amino acid residue positions. The numbers to the right indicate nucleotide residue positions. Amino acids are designated by the single-letter code, and * indicates the termination codon. The boxed sequences identify possible N-linked glycosylation sites. Hydrophobic regions that may identify signal and transmembrane peptides are underlined. The vertical arrow marks the most probable position of the amino-terminus of the mature protein. (See von Heijne, Nucleic Acids Res. 14:4683 (1986)).

The amino acid sequence of LAM-1 predicted a structure typical of a membrane glycoprotein. Two potential translation initiation sites were found at nucleotide positions 53 and 92. The second initiation site conformed best to the consensus sequence for optimal initiation (A/G)CCAUG (Kozak, Cell 44: 283–292 (1986)) and was followed by a hydrophobic region of 27 amino acids that may represent a signal peptide. The algorithm of von Heijne predicted that the most probable amino-terminus of the mature protein would be the Trp at amino acid position 52. The LAM-1 sequence contained a second hydrophobic region between amino acids 346–368 which may be a transmembrane region. The deduced mature LAM-1 protein would have an extracellular region of about 294 amino acids containing 7 potential N-linked carbohydrate attachment sites. LAM-1 would have a cytoplasmic tail of 17 amino acids containing 8 basic and 1 acidic residues. The two cytoplasmic Ser residues may serve as substrates for phosphorylation since protein kinase C phosphorylates Ser residues that are on the carboxyl-terminal side of several basic residues. These results suggest that the processed LAM-1 protein would have a Mr of at least 50,000. The LAM-1 protein can be isolated by conventional techniques, such as affinity column chromatography with antibody or ligand, from cell lines that normally express this receptor or from transfected cell lines. Or the protein can be synthesized by in vitro translation of the LAM-1 cDNA.

Figure 3A:
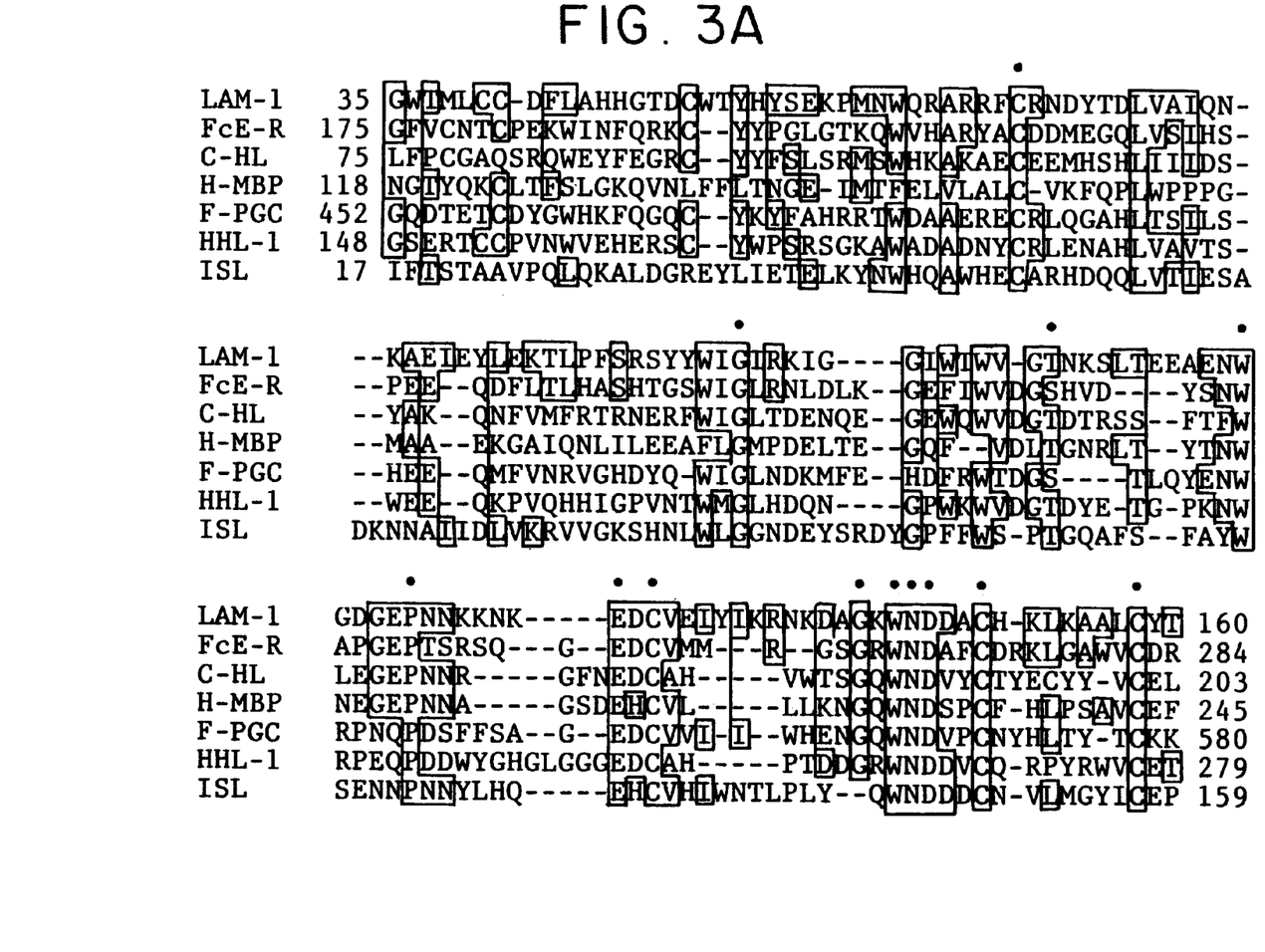
FIGS. 3A, 3B and 3C show the homologies of LAM-1 with other proteins.
Figure 3B:
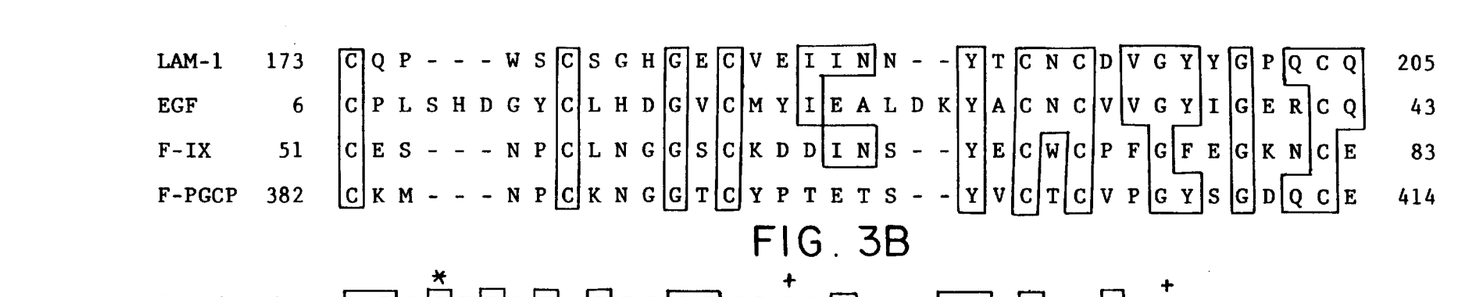
Figure 3C:
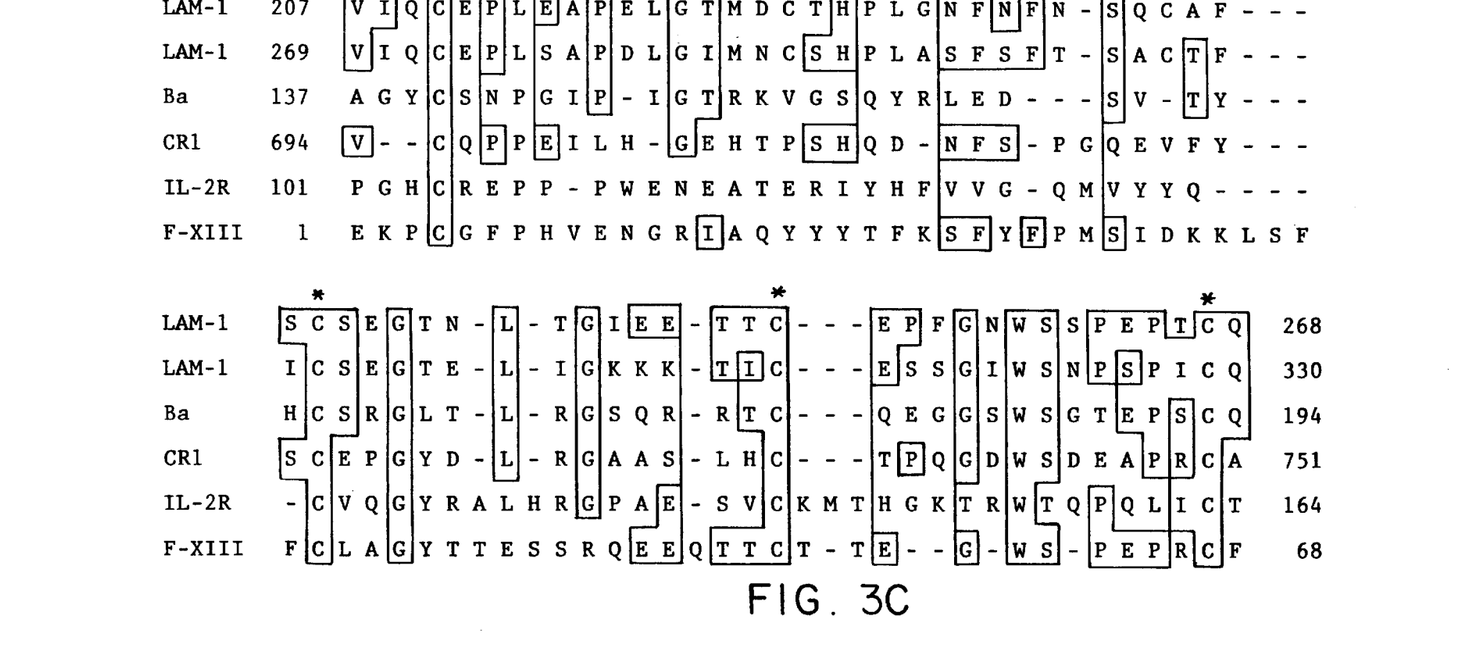

LAM-1 combines previously unrelated domains found in three distinct families of molecules: animal lectins, growth factors, and C3/C4 binding proteins. The proposed extracellular region of LAM-1 contained a high number of Cys residues (7%) with a general structure as diagrammed in FIG. 1B. As indicated in FIG. 3, segments of homologous proteins are shown with the amino acid residue numbers at each end. Homologous amino acids are shown in boxes. Gaps (–) have been inserted in the sequences to maximize homologies. The first 157 amino acids of the protein (FIG. 3A) were homologous with the low-affinity receptor for IgE (Kikutani et al., Cell 47:657 (1986)), the asialoglycoprotein receptor (Spiess et al., Proc. Natl. Acad. Sci. USA 82:6465 (1985)) and several other carbohydrate-binding proteins (Drickamer et al., J. Biol. Chem. 256:5827 (1981); Ezekowitz et al., J. Exp. Med. 167:1034 (1988); Krusius et al., J. Biol. Chem 262:13120–13125 (1987); and Takahashi et al., J. Biol. Chem. 260:12228 (1985)). The amino acids conserved among all animal-lectin carbohydrate recognition domains are indicated (*). Although the sequence homologies were less than 30%, all the invariant residues found in animal lectin carbohydrate-recognition domains were conserved (Drickamer, J. Biol. Chem. 263:9557 (1988)).

The next domain of 36 amino acids (FIG. 3B) was homologous (36–39%) with epidermal growth factor (EGF) (Gregory, Nature 257:325 (1975)) and the EGF-like repeat units found in Factor IX (Yoshitake et al., Biochem. 25:3736 (1985)) and fibroblast proteoglycan core protein (Krusius et al., supra).

Immediately following these domains were two tandem domains of 62 amino acids each (FIG. 3C) that were homologous with the short consensus repeat units (SCR) that comprise the IL-2 receptor (Leonard et al., Nature 311:626 (1984)), Factor XIII (Ichinose et al., Biochem. 25:4633 (1986)) and many C3/C4 binding proteins (Klickstein et al., J. Exp. Med. 165:1095 (1987); and Morley et al., EMBO J. 3:153 (1984)). In contrast with all of the previously described SCR that contain four conserved Cys residues, these two SCR possessed six Cys residues. The four conserved Cys residues found in all SCR are indicated in FIG. 3C by (*); the additional conserved Cys found in LAM-1 are indicated by (+). Of the multiple SCR present in each of these proteins, the SCR with the highest homology to LAM-1 is diagrammed. A 15 amino acid spacer preceded the putative transmembrane domain.

The deduced amino acid sequence of LAM-1 is homologous with that of ELAM-1 and GMP-140. Thus these two proteins and LAM-1 define a new family of homologous structures that are expressed by different cell lineages and that can function as receptors in cellular interactions.

Use

As lymphocyte migration and infiltration into areas of tissue damage or injury or tissue transplant can cause or increase pathology, agents that impede these processes can be used for therapeutic treatment. LAM-1 can be used as an antigen to produce antibodies against this protein and to develop antagonistic ligands that can interfere with lymphocyte adhesions and function. The use of these reagents in research will permit the determination of the 3-dimensional structure of LAM-1 and clarify its role in lymphocyte function. The administration of these reagents to patients can be used to block or reduce pathology. As an example, subpopulations of malignant cells that express this antigen would allow the receptor to function in metastasis of tumor cells. Agents developed to block receptor function can inhibit the metastasis and homing of malignant cells.

Other embodiments are within the following claims.

I claim:

1. An isolated and purified DNA molecule encoding a human LAM-1 protein having the amino acid sequence shown in FIG. 2.

2. The DNA molecule according to claim 1, wherein the DNA molecule comprises the DNA sequence set forth in FIG. 2.

3. A recombinant DNA molecule comprising a DNA molecule encoding a human LAM-1 protein having the amino acid sequence shown in FIG. 2, operatively linked to an expression control sequence.

4. A host cell comprising a DNA molecule encoding a human LAM-1 protein having the amino acid sequence show in FIG. 2.

5. A host cell according to claim 4 expressing a human LAM-1 protein having the amino acid sequence shown in FIG. 2.

6. A host cell comprising a DNA molecule encoding a human LAM-1 protein having the amino acid sequence shown in FIG. 2, operatively linked to an expression control sequence.

7. A host cell according to claim 6 expressing a human LAM-1 protein having the amino acid sequence shown in FIG. 2.

8. A method for producing a human LAM-1 protein having the amino acid sequence shown in FIG. 2, comprising the step of culturing a host cell according to any one of claims 4, 5, 6, or 7.

* * * * *